(12) United States Patent
Nelson

(10) Patent No.: US 8,538,728 B2
(45) Date of Patent: Sep. 17, 2013

(54) RADIO-NUCLIDE MIXTURE IDENTIFICATION USING MEDIUM ENERGY RESOLUTION DETECTORS

(75) Inventor: Karl Einar Nelson, Livermore, CA (US)

(73) Assignee: Lawrence Livermore National Security, LLC, Livermore, CA (US)

(*) Notice: Subject to any disclaimer, the term of this patent is extended or adjusted under 35 U.S.C. 154(b) by 365 days.

(21) Appl. No.: 12/770,215

(22) Filed: Apr. 29, 2010

(65) Prior Publication Data
US 2011/0270575 A1 Nov. 3, 2011

(51) Int. Cl.
G06F 17/18 (2006.01)
G06F 17/10 (2006.01)
G21C 17/04 (2006.01)
G01T 1/36 (2006.01)

(52) U.S. Cl.
USPC ............. 702/181; 703/2; 250/370.03; 378/83

(58) Field of Classification Search
USPC ......... 702/181, 23, 26–32, 40, 66–67, 70–73, 702/75–76, 78, 81, 84, 179–180, 182–183, 702/189–190, 196; 703/2, 5, 12; 250/370.03, 250/370.05, 370.09, 370.11, 390.02, 390.04, 250/390.07, 390.11; 378/4–5, 82–83, 86, 378/88
See application file for complete search history.

(56) References Cited

U.S. PATENT DOCUMENTS
2011/0270536 A1* 11/2011 Nelson ............................ 702/30

OTHER PUBLICATIONS

Gosnell, T., Automated Calculation of Photon Source Emission from Arbitrary Mixture of Naturally Radioactive Heavy Nuclides, 1990, Nuclear Instruments and Methods in Physics Research A 299, pp. 682-686.*
Roemer et al., Simulation of Template Spectra for Scintillator Based Radionuclide Identification Devices Using GEANT4, 2006 IEEE Nuclear Science Symposium Conference Record, pp. 247-252.*
Burr et al., Radio-Isotope Identification Algorithms for NaI Gamma Spectra, Mar. 3, 2009, Algorithms 2009, pp. 339-360.*
O. Marzocchi, Automation of a Gamma Spectrometric Analysis Method for Naturally Occuring Radionuclides in Different Materials (NORM), Jun. 2009, Institut fur Strahlenforschung, 92 pp.*
Non-Final Office Action Summary from U.S. Appl. No. 12/770,260 dated Feb. 17, 2012.
Non-Final Office Action Summary from U.S. Appl. No. 12/770,260 dated Jul. 24, 2012.
Arnold, et al., "The 2002 IAEA Intercomparison of Software for Low-Level Gamma-Ray Spectrometry," 2005, Nuclear Instruments and Methods in Physics Research A 536, pp. 196-210.
Notice of Allowance and Fee(s) Due from U.S. Appl. No. 12/770,260 dated Dec. 13, 2012.

* cited by examiner

Primary Examiner — Toan Le
(74) Attorney, Agent, or Firm — Dominic M. Kotab

(57) ABSTRACT

According to one embodiment, a method for identifying radio-nuclides includes receiving spectral data, extracting a feature set from the spectral data comparable to a plurality of templates in a template library, and using a branch and bound method to determine a probable template match based on the feature set and templates in the template library. In another embodiment, a device for identifying unknown radio-nuclides includes a processor, a multi-channel analyzer, and a memory operatively coupled to the processor, the memory having computer readable code stored thereon. The computer readable code is configured, when executed by the processor, to receive spectral data, to extract a feature set from the spectral data comparable to a plurality of templates in a template library, and to use a branch and bound method to determine a probable template match based on the feature set and templates in the template library.

21 Claims, 2 Drawing Sheets

RADIO-NUCLIDE MIXTURE IDENTIFICATION USING MEDIUM ENERGY RESOLUTION DETECTORS

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to radio-nuclide identification, and particularly, to radio-nuclide identification using medium energy resolution detectors.

BACKGROUND

Most nuclide identification algorithms either use peak extraction and an expert tree system or full template matching techniques. Peak extraction with an expert tree works reasonably well with high energy resolution detectors or scintillators (HPGe), but is less effective on low to mid energy resolution scintillators. Template matching makes better use of the information available, but requires solving a potentially massive optimization problem. As a result, all template matching algorithms depend on heuristics to reduce the required computation. These heuristics have the significant downside that they can miss the optimal solution entirely. In addition, mixtures of radio-nuclides have notoriously been difficult to identify with conventional techniques due to several factors, including the limitations on including mixtures in spectrum libraries and misidentification of mixtures.

Therefore, it would be beneficial to the field of radio-nuclide identification to be able to identify mixtures of radio-nuclides with low to mid energy resolution detectors, such as scintillators, that are capable of avoiding the problems associated with conventional techniques.

SUMMARY

In one embodiment, a method for identifying one or more radio-nuclides includes receiving spectral data, extracting a feature set from the spectral data comparable to a plurality of templates in a template library, and using a branch and bound method to determine a probable template match based on the feature set and templates in the template library.

In another embodiment, a device for identifying one or more unknown radio-nuclides includes a processor, a multi-channel analyzer, and a memory operatively coupled to the processor, the memory having computer readable code stored thereon. The computer readable code is configured, when executed by the processor, to receive spectral data, to extract a feature set from the spectral data comparable to a plurality of templates in a template library, and to use a branch and bound method to determine a probable template match based on the feature set and templates in the template library.

In another embodiment, a computer program product for identifying one or more unknown radio-nuclides includes a computer readable storage medium having computer readable code stored thereon. The computer readable code comprises computer readable code configured to receive spectral data, computer readable code configured to extract a feature set from the spectral data comparable to a plurality of templates in a template library, and computer readable code configured to use a branch and bound method to determine a probable template match based on the feature set and templates in the template library.

Other aspects and embodiments of the present invention will become apparent from the following detailed description, which, when taken in conjunction with the drawings, illustrate by way of example the principles of the invention.

DETAILED DESCRIPTION

Figure 1:
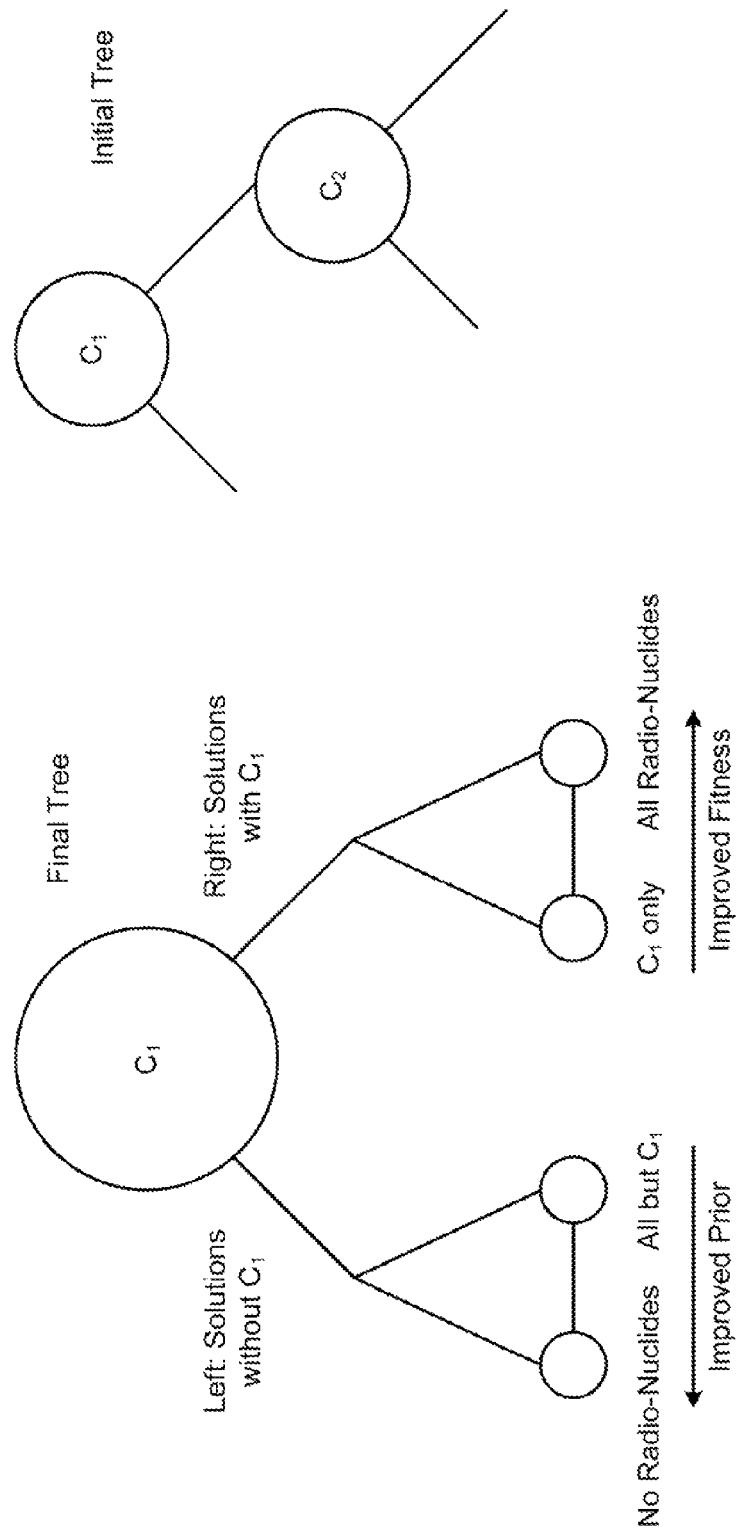
FIG. 1 is a schematic diagram of an example of a complete decision tree and an initial tree, according to one embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

As used herein, the term "about" when combined with a value refers to plus and minus 10% of the reference value unless otherwise specified. For example, a temperature of about 50° C. refers to a temperature of 50° C.±5° C., etc.

Disclosed herein, according to some embodiments, is a modification to the branch and bound algorithm which effectively eliminates problems associated with conventional techniques while keeping the size of computations used in the method to a minimum. The branch and bound algorithm was found to be a suitable method when combined with Bayesian statistics. This is a significant improvement over conventional techniques to the handling of mixtures for nuclide identification.

In one general embodiment, a method for identifying one or more radio-nuclides includes receiving spectral data, extracting a feature set from the spectral data comparable to a plurality of templates in a template library, and using a branch and bound method to determine a probable template match based on the feature set and templates in the template library.

In another general embodiment, a device for identifying one or more unknown radio-nuclides includes a processor, a multi-channel analyzer, and a memory operatively coupled to the processor, the memory having computer readable code stored thereon. The computer readable code is configured, when executed by the processor, to receive spectral data, to extract a feature set from the spectral data comparable to a plurality of templates in a template library, and to use a branch and bound method to determine a probable template match based on the feature set and templates in the template library.

In another general embodiment, a computer program product for identifying one or more unknown radio-nuclides includes a computer readable storage medium having computer readable code stored thereon. The computer readable code comprises computer readable code configured to receive spectral data, computer readable code configured to extract a feature set from the spectral data comparable to a plurality of templates in a template library, and computer readable code configured to use a branch and bound method to determine a probable template match based on the feature set and templates in the template library.

According to some embodiments, a method for identifying single radio-nuclides from low-resolution gamma-ray spectra of the types obtained from hand-held instruments used by first responders can be achieved. However, complex radio-nuclides are more difficult to identify, and therefore a method of identifying complex radio-nuclides while using low-resolution gamma-ray spectra of the types obtained from hand-held instruments used by first responders would be very valuable. In some approaches, the method may include identification of complex mixtures of radio-nuclides in a wide variety of configurations.

Radio-Nuclide Identification

Given a histogram of photon energies from a radiation detector, such as a scintillator, it can be difficult to identify the emitted radio-nuclides which best fit the measurements. Mixtures are possible between different radio-nuclides, and the source material may be shielded by a range of different intervening attenuators.

Bayesian View

In one approach, to solve this problem, a model $\Theta$ which maximizes the quantity $P(\Theta|Y)$ for an observation where $Y=[y_i]$. Bayes' rule can be used to transform this quantity into a value computed as shown in Equation 1.

$$P(\Theta|Y) = \frac{P(Y\Theta)}{P(Y)} = \frac{P(Y|\Theta)P(\Theta)}{P(Y)} \quad \text{Equation 1}$$

In Equation 1, $P(\Theta)$ is the prior probability of finding a source of a given model in the absence of evidence, $P(Y)$ is a model independent probability of producing this observation, and $P(Y|\Theta)$ is the probability of producing this observation from this model. We can generally ignore the term $P(Y)$ (the probability of the observation) as it does not change the ranking of the solutions. The probability of the observation being produced by the model is given by the statistics of the radiation transport processes which produced the radiation. For Poisson statistics, Equation 2 can be used to compute the expected spectra given the model $F=[f_i]$.

$$P(Y|\Theta) = \prod_i \frac{f_i^{y_i} e^{-f_i}}{y_i!} \quad \text{Equation 2}$$

However, in practice, the channel variances are both a function of the Poisson variance, calibration uncertainty, and modeling errors, and it was assumed that Gaussian statistics can be applied instead. For a channel variance estimate $\sigma_i^2$, the observation probability can be computed as shown in Equation 3.

$$P(Y|\Theta) = \prod_i \frac{1}{\sqrt{2\pi\sigma^2}} \exp\left(\frac{-(y_i - f_i)^2}{2\sigma_i^2}\right) \quad \text{Equation 3}$$

This leaves the probability of the model $P(\Theta)$. The model is composed of a set of different radio-nuclides, according to the assumption. If these radio-nuclides were each independent, then a probability could be assigned to each $P(N_i)$. However, not all radio-nuclides are independent, for example parent daughter chains, in which case the probabilities are joint, as represented by $P(N_p \cap N_d)=P(N_p)P(N_d)+C(N_p N_d)$. For simplicity of expressing equations, the independent formulation will be used. The a priori probability of observing any particular nuclide is generally small (e.g., less than about 10%), thus the a priori probability of not observing the particular nuclide, which is one minus the probability of observing it, is generally large (e.g., greater than about 90%).

For nuclides that are part of the natural background, such as $^{232}$Th, $^{40}$K, and $^{22}$Ra, the nuclides are expected to be in any sample measured, thus making the a priori probability 100% of finding them in a sample. However, as the background nuclides may be overshadowed by other nuclides, a lower prior probability of 50% is a better choice for the calculations, in that there would be no penalty for either including or excluding a background nuclide from the mixture with this probability selection.

Therefore, the maximum probability will be the probability of observing no nuclides, as expressed in Equation 4.

$$\prod_i P(\overline{N}_i) = \prod_i (1 - P(N_i)) \quad \text{Equation 4}$$

The probability of observing a single nuclide $N_j$ would be calculated through Equation 5.

$$P(N_j) \prod_{i \neq j} (1 - P(N_j)) \quad \text{Equation 5}$$

For some radio-nuclides, such as those which are commonly found in background spectra, the prior probability of the radio-nuclide is large (as previously discussed, 0.5). All others will be small (<0.01).

Finally, to simplify the mathematics, it is common practice to compute these probabilities in the log space. This is referred to as the log likelihood. The decision to include or exclude a particular radio-nuclide is represented by the binary variable $u_i$. All of the factors which are not a function of the model are lumped together in the single factor $\kappa$ which can be ignored. Therefore, the calculation for the log likelihood can be expressed as shown in Equation 6.

$$\ln P(\Theta|Y) = \quad \text{Equation 6}$$
$$K - \frac{1}{2}\sum_j \frac{(y_i - f_j)^2}{\sigma_j^2} + \sum_i u_i \ln P(N_i) + (1 - u_i)\ln 1 - P(N_i)$$

Usually, at this point, an immediate objection can be raised that the prior probability of finding some model is not known. Therefore, an assumption would be made at some point, and this will bias the results. Although it is true that an assumption has generally been made to assign these probabilities, it is necessary and good scientific practice to do so. The Bayesian priors are simply a restatement of Occam's razor. The more radio-nuclides that are required, the greater the penalty that must be overcome with evidence. That is the improvement in $P(Y|\Theta)$, which must be greater than the penalty of $P(N_i)/(1-P(N_i))$. Though there is no guarantee that the more complex solution is not the correct one, simpler solutions are generally preferred and often times correct.

Formulation of Mixture Analysis

Thus far, the probabilistic terms of the problem have been defined, but more mechanical portions have yet to be addressed. A set of radio-nuclides are present which are to be matched to an observation. Thus, a representation of the radio-nuclide itself is required. To accomplish this, a set of templates for each radio-nuclide is created. The templates for a given nuclide $N_i$ will be stored in a matrix $A_i$. The templates are designed to span the range of variability such that for a certain number of source counts, all possible spectra have a probability in the absence of noise less than some predetermined small factor $\in$.

Using this template library, the expected spectrum F(u) can be expressed as being computed as shown in Equation 7:

$$F(u) = \sum_i u_i A_i x_i \qquad \text{Equation 7}$$

where $x_i$ is a set of nuisance parameters which are calculated to maximize $P(Y|\Theta)$. Thus, the goal is to find the set of binary inclusion variables u and real nuisance variables $x_i$ which minimize The objective function, as shown in Equation 8.

$$H(u, x) = \frac{1}{2}\left(Y - \sum_i u_i A_i X_i\right)^T \sum^{-1}\left(Y - \sum_i u_i A_i X_i\right) - \qquad \text{Equation 8}$$

$$\sum_i u_i \ln P(N_i) - (1 - u_i)\ln 1 - P(N_i)$$

Typically, we are interested in analyzing up to 100 different potential radio-nuclides in combination. This results in $2^{100}$ different possible combinations (roughly $10^{30}$). This would be practically impossible to search in a reasonable length of time using brute force techniques. As a result, most approaches develop a heuristic method to the problem. These heuristics can often find a good solution to the problem. Unfortunately, their efficiency comes at a cost, as they are not guaranteed to find the optimum solution.

The common heuristic to solve this problem is to assume a set of radio-nuclides which could commonly be found together. Then, some subset which minimizes the square error is found. However, this solution is often overly complex, so radio-nuclides are removed starting with the least contributing in terms of total number of counts. The reducing is continued so long as the increase in probability resulting from removal of the radio-nuclides is greater than the resulting loss in the quality of the fit. Unfortunately, this algorithm has a pitfall. Each time the least contributing component is removed, the assumption that the most contributing component is the best fit is reinforced. As a result, the algorithm will often settle in some local minima, and thus the global optimum is missed. To compensate for this tendency, this process may be repeated for several common subsets, in effect giving multiple starting points from which the optimum may be found. Assuming N nuclides and M subsets, the required computation may be estimated. Depending on whether the reduction is performed one nuclide at a time or en masse, the number of actual optimization problems can range from the number of subsets attempted O(M) to the product of the number of subsets and the nuclides O(NM).

However, there is a class of algorithms that can solve these sorts of problems with good efficiency using the principle of inequalities combined with the principle of divide and conquer. This algorithm is called branch and bound. The algorithm depends on two basic tenets. First, the variables are organized into a tree such that similar solutions lie close to each other such that possibilities can be dismissed en masse when a fit is not seen. Second, the bound of the objective function is estimated based on subsets of candidates of similar solutions. Both of these objectives can be accomplished for this particular problem. The binary inclusion variables can be organized into a tree. Starting with the decision to include or exclude a single radio-nuclide, all possible solutions can be viewed as either containing or excluding the radio-nuclide. By selecting the order of these decisions, the subsets can be organized such that similar solutions are clustered together. Further, an inequality can be used to bound the solutions which lie down a particular branch. This inequality is that probability of the observation that produced a model including one set of nuclides $P(Y|\Theta_1)$ must be less than or equal to the probability of the observation being produced by a superset containing that set and some additional members $P(Y|\Theta_1) \leqq P(Y|\Theta_1+\Theta_2)$.

Branch and Bound

As all of the elements to formulate a branch and bound algorithm are met, the algorithm can also be formalized. There are two requirements to use a branch and bound method according to one embodiment similar solutions with similar fitness are organized into a binary tree for ease of use, and it is possible to define an inequality such that knowledge about a superset can be used to estimate (and thus rule out) subsolutions that lie further down the tree. The root of the tree has a pivot radio-nuclide which represents the decision to include or exclude one of the variables. By convention, the left hand side excludes the pivot radio-nuclide and the right hand side includes the variable. Each level of the tree includes another pivot all the way down to the leaves of the tree where all of the decision variables are fixed as either included or excluded. The organization of this tree is arbitrary, but there is a natural order to optimize the efficiency of searching. The pivot variables do not have to appear in the same order on both sides of the tree. In some approaches, this fully populated version of the tree is not implemented. Instead, in some approaches, branches of this tree are ruled out using an inequality. The maximum fitness of all solutions at the left size of a tree is known, as $P(Y|\theta_d \not\in \Theta)$ is less than or equal to the maximum fitness of all solutions on the right side of the tree $P(Y|\theta_d \in \Theta)$. This inequality is true for each level of the tree. Thus, the probability of the best possible solution on the left hand side can be computed as shown in Equation 9.

$$\left(\operatorname*{argmax}_{\theta_d \not\in \Theta} P(\Theta)\right) P(Y | \theta_d \not\in \Theta) \leq \left(\operatorname*{argmax}_{\theta_d \not\in \Theta} P(\Theta)\right) P(Y | \theta_d \in \Theta) \qquad \text{Equation 9}$$

Similarly, it is known that the best possible solution on the right side is the best possible probability with $\Theta_d$ included times the max fitness of the right most branch. The decision to explore the left hand side or the right hand side simply becomes a question of whether the best solution on either branch is better than the best solution that has been found thus far.

The key to efficiency in this process is to choose the organization of the tree such that as many possibilities can be dismissed as early as possible. There are at least two ways to accomplish this goal. A first method is to establish a good solution early in the process. The sooner a good solution is obtained, the more branches can be trimmed off. This concept of finding a good solution first will be explored more fully later. Another method is to arrange the decision tree in such a way that solutions which are most similar are arranged together.

In one arrangement, the tree is organized such that the decision variable is given by the largest contributor in the best fitness right hand solution that has not already been decided by the parent. In the second arrangement, the decision variable for this node is given by the least contributing component in the best fitness right hand solution. In the latter case, the optimum solution and the optimum solution containing trivial amounts of another radio-nuclide are on different sides of the root node. Thus, the best and second best solutions are widely separated. As a result, the optimization algorithm will likely need to explore down both sides of the tree to decide which one is best. In the former case, the best and second best solutions share the same parent at the bottom of the tree. Thus the former method of arranging the tree based on the largest contributor will place similar solutions close together and consequently be a better organization strategy. Though there is no guarantee that the largest component will make the largest difference in terms of the quality of fitness, it is a best guess.

Thus far, it has been established how the tree is to be organized and how it will be used to rule out solutions. Thus, a remaining task is to create the tree. Referring to FIG. 1, in integer programming problems, the first step is to solve the problem in an unconstrained fashion. For this problem, a solution is equivalent to solving the quadratic problem with all of the templates included. This first solution is overly complex but has the best possible fitness that can be achieved. The probability of this solution will thus be quite low. However, this establishes the first lower bound as the best known solution. With this solution, the most contributing component $C_1$ and the second most contributing component $C_2$ are found. The most contributing component is the decision variable for the root node and the second most contributing component is the decision variable for the right hand side. This is shown in FIG. 1. At this point, a strategy is set for which node is explored first. The highest prior probability solution is in the branch on the left hand side of $C_1$ corresponding to the solution with background only. The most likely good solution given the initial fit is the solution that contains $C_i$ only and is on the left hand branch of $C_2$. The choice of which way to proceed is arbitrary, but some assumptions can guide this decision. In radio-nuclide identification, it is generally assumed that there was a good reason of analyzing the spectrum in the first place. The person taking the spectrum or the alarming algorithm which selected this sequence of data for analysis did so because there was some evidence of a presence of a radiation source. As such, it is assumed that the left most leaf node of $C_1$ is unlikely to ultimately be the best solution. Thus, the search procedure is started on the right side of the root node.

There are several possible methods to explore the tree. Illustrative strategies include a depth first search and a greedy search. The depth first search approach descends the tree until either a leaf is hit ox a branch is ruled out. Then, ascend out of each node to either rule out the other branch or explore it. It may be best to explore the left band branch as the tree is descended first as the maximum possible probability given for the left side will be greater than the right under the assumption that $P(\overline{\theta}_1) > P(\theta_j)$. This method also is efficient for a quadratic solver, as partial solutions computed for the parent node can be reused to seed the solution. One alternative approach would be to keep a list of open nodes and explore them based on the highest estimated probability. The greedy assumption would be the same algorithmic approach as used in the A* algorithm. The A* algorithm is an algorithm with similar assumptions. It is used in automotive navigation to find the best path from one place to another on a graph problem. For the present problem, this approach has the downside that a performance penalty is incurred with the quadratic solver as jumps are taken around the tree. This performance penalty can be reduced by having a finite set of quadratic solvers which hold the solutions at intermediate points in the tree. At the current time, it is not clear which method is the best approach, though all should provide adequate results. Thus, as the depth first search is less complex to program, it has been implemented. The algorithm is summarized in pseudo-code shown below.

```
SolutionRoot=Solve with all u_i=1
Best=Prior(SolutionRoot) times Fitness(SolutionRoot)
Contributor1=Find largest contributor in SolutionRoot
Contributor2=Find second largest contributor in SolutionRoot
Node1=Insert node with Contributor1
Node2=Insert node in Contributor2 on Node1 left
Explore(Node2, SolutionRoot)
Explore(Node1, SolutionRoot)
SUBROUTINE Explore(Node, Solution)
   IF (Node does not have left) THEN
      SolutionLeft=Solve without variable given by Node
      ProbMaxLeft=Max Prior Node without variable
      ContributorLeft=Max free contributor of Solution Left
   IF (Prior(SolutionLeft)*Fitness(SolutionLeft)) THEN
      Best=Prior(Solution Left)*Fitness(SolutionLeft)
   IF (ProbMaxLeft*Fitness(SolutionLeft)>best) THEN
      NodeLeft=Insert node with CL on left of Node
      Explore (NodeLeft, Solution Left)
   IF (Node does not have right) THEN
      ProbMaxRight=Max Prior Node with variable
   IF (PriorMaxRight*Fitness(Solution)) THEN
      NodeRight=Insert node with CL on right of Node
      Explore(NodeRight, Solution)
END SUBROUTINE
```

This pseudo-code may be used for radio-nuclide identification using a branch and bound algorithm, according to one embodiment. The algorithm first solves the unconstrained problem to establish the start of the tree and to establish the best known solution.

Improving the Decision Process

In evaluating this algorithm, there were potential improvements to the search algorithm available. In particular, much time was spent descending to the left to solve the quadratic problem to find the next decision variable. However, at the same time, only the leftmost leaf of the tree was often of interest. Therefore, populating these intermediate nodes can be avoided by computing not just the best prior in the left branch, but also the second best possible prior. If the best prior times the current fitness is better than the best found solution but the second best prior times the current fitness is not, then skipping to the leaf node is prudent and all the intermediate decision nodes can be dropped. Furthermore, by always solving the leftmost leaf node upon entry to the node, the algorithm can be improved further. As the leftmost node has the maximum prior probability, it is also likely to improve the best found solution and then rule out the second best solution preventing the need to further explore the left branch. This logic can, in principle, improve performance, especially when the number of decision variables considered is large.

Quadratic Solver

Coupled with this optimization algorithm is an algorithm to solve the quadratic problem of constructing the best fit with all positive constraints. A number of potential algorithms have been considered. All have a similar structure. In each, it is assumed that the best combination contains none of the regressors and solves to find the residual. Each algorithm then selects one or more of the unused regressors to add to the solution and resolves. If any regressors have a negative weight, they are dropped. This process repeats until no further improvement is possible. The best performing algorithm, according to one embodiment, is a greedy algorithm with several speed optimizations. As the bigger picture of the optimization is being handled by the branch and bound algorithm, the most compact subset does not need to be sought. The global optimum for the branch is used to ensure that the inequality always holds and thus the subset regression algorithms that stop prior to finding the global optimum, such as stepwise regression, are not well suited. Further, the extra time spent finding the optimum regressor to add at each iteration is not worth the time compared to greedily adding the regressor with the largest projection on the current residual. In addition, a block pivot algorithm which selects all of the variables which have a positive projection on residual has been considered. This algorithm proved numerically problematic as often combinations of regressors were linearly dependent. Thus, regressors were added one at a time.

Based on this process, the algorithm should both use the cheapest method to identify the next regressor to add and should add and remove regressors individually. However, this still leaves the possibility of cycles. Occasionally, adding the largest projecting regressor will cause another regressor to become negative, which in turn removes another regressor, and so on, until ultimately the algorithm removes the need for the largest projecting regressor. The algorithm can become stuck in these cycles. Thus two cycle busting rules have been added. The first rule is that any regressor which when added results in removing itself without an "add" in between shall be poisoned and removed from the list of candidates. Second, at each step of the process, a list of the sequence of "adds" and "removes" is maintained. If, whenever a candidate is added which was previously in the solution, the audit log is checked to see if the sequence of resulting removes matches the sequence of removes when the regressor was last added. If the same sequence occurred, then this regressor causes a cycle and is be poisoned. Whenever a regressor is poisoned, the audit log can be used to push back in those regressors which had been incorrectly removed.

In initial testing, the largest time consumer in this procedure was the Gauss reduction step used to solve the inverse $O(N^3)$. The cost of this step can be reduced by storing the problem in QR form. QR is a representation of a matrix as a rotation matrix multiplied by an upper triangular matrix. It is the result of a QR factorization which is commonly used to solve a least squares problem. So long as the QR factorization is maintained, the cost of the inverse is $O(N^2)$. The process of building up the QR factorization increases the overall cost to be the same at Gauss reduction. However, as the QR factorization can be reused as new regressors are added and removed from the solution set, the overall cost of the algorithm drops considerably. Further, the QR factorization can be maintained throughout the branch and bound algorithm and thus, as the tree is being descended, a reduced overall cost is maintained.

Once the QR factorization was applied, a dominant cost became computing the projection of each potential regressor on the residual. As there may be many more candidate regressors than will ever be used in any individual solution, this step grows increasingly large as the number of radio-nuclides to be identified increases. To aid in this problem, the candidates can be split into two categories. When evaluating the projection of the regressor on the residual, if this projection was negative, then this candidate is transferred to a deferred group and will not be considered again until there are no remaining active candidates. This did not affect the ability to find the global minimum and at the same time reduced the number of cycles. The resulting algorithm required only 15% of the number of multiplies compared to an original algorithm.

The final optimization, in one approach, is the QR factorization. In a normal QR factoration, the Gauss-Jordan sweep operator is applied to all of the candidate regressors whenever a regressor is added or removed. Mathematically, the inverse of the projection of the current in regressors $(X'\Sigma^{-1}X)$ is desired out of the possible candidate regressors (Y) for which a matrix Z as shown in Equation 10 is maintained. Matrix Z is referred to as the design and data matrix and is equal to the cross product matrix $(Z=Y'\Sigma^{1}Y)$ prior to the first pivot operation. However, as there are many more candidates than the number of regressors which will ever be used in the solution, this operation increased the cost of the inverse operation once the number of the candidates were sufficiently large. Thus, rather that applying the Guass-Jordan sweep to the entire set, the existing solution was augmented $(Z=-(X'\Sigma^{-1}X)^{-1})$ with the single new regressor as if the Gauss-Jordan operation had been maintained all along. The cost of augmenting is that $(X'\Sigma^{-1}X)^{-1}X'\Sigma^{-1}Y$ is computed. This optimization had the added benefit that lazy evaluation could be used when computing the cross product matrix. Thus, rather than computing the entire cross product matrix, only those elements that were required were computed, as shown in Equation 10.

$$Z = \begin{bmatrix} -(X'\Sigma^{-1}X)^{-1} & (X^1\Sigma^{-1}X)^{-1}X'\Sigma^{-1}Y \\ Y'\Sigma^{-1}X(X'\Sigma^{-1}X)^{-1} & Y'\Sigma^{-1}Y - Y'\sum^{-1} X(X^1\Sigma^{-1}X)^{-1}X'\Sigma^{-1}Y \end{bmatrix}$$

Equation 10

Results

To evaluate the performance of this algorithm on a realistic problem, 1000 samples were created of random mixtures of radio-nuclides. Samples were created synthetically using the Gamma Detector Response and Analysis Software (GADRAS) response suite. GADRAS is a U.S. government simulation program used to produce synthetic spectrum, and therefore any simulation software may be used to reproduce these results. The simulated detector was a standard 2"×4"×16× NaI(Tl) detector. Samples contained up to three radio-nuclides selected from Table 1. For each radio-nuclide, a shielding was selected from a list of possible atomic numbers. A corresponding shielding thickness in terms of areal density was selected. The resulting configuration was then scaled to have between about 500 and about 2500 counts uniformly distributed. This was then summed with a representative background. To give a fair basis for comparison, this same sample set was run through the identification routine provided in GADRAS. The shielding conditions were selected to be within the defined problem space of the GADRAS identification routine, and all extra nuclides not used in the test were removed to reduce the possibilities of errors. Fissile materials have also been removed as they are inherently mixtures and require special scoring. This mixture problem is far harder than any other that has been found described in literature and thus represents a serious challenge to any radio-nuclide identification algorithm. The error rate for GADRAS was 266 false inclusion errors and 145 false exclusion errors. A total of 300 samples contained an error. Given the difficulty of the problem, this is a very respectable score. This is considerably better than the error rate (46%) reported using Adaptive Learning Image and Signal Analysis (ALISA) on an unshielded set of radio-nuclides. The full report may be found in the report: "Using ALISA for high-speed classification of the components and their concentrations in mixtures of radio-isotopes," Proc. SPIE, Vol. 5541, 1 (2004).

TABLE 1

| Radio-Nuclide | Shielding Z | Shielding Areal Density (g/cm$^2$) |
|---|---|---|
| $^{241}$Am | (7, 26, 50, 82) | (30, 30, 20, 10) |
| $^{133}$Ba | (7, 26) | (30, 30, 30, 30) |
| $^{207}$Bi | (7, 26) | (10, 10) |
| $^{57}$Co | (7, 26, 50, 82) | (10, 10) |
| $^{60}$Co | (7, 26, 50, 82) | (30, 30, 60, 100) |
| $^{137}$Cs | (7, 26, 50, 82) | (30, 30, 60, 100) |
| $^{152}$Eu | (7, 26, 50, 82) | (10, 10, 20, 20) |
| $^{154}$Eu | (7, 26, 50, 82) | (10, 10, 20, 20) |
| $^{67}$Ga | (7, 26, 50, 82) | (20, 20, 10, 10) |
| $^{166m}$Ho | (7, 26, 50, 82) | (20, 20, 30, 30) |
| $^{131}$I | (7, 26) | (50, 30) |
| $^{111}$In | (7, 26, 50) | (20, 20, 20) |
| $^{192}$Ir | (7, 26, 50, 82) | (30, 30, 50, 100) |
| $^{138}$La | (7, 26, 50) | (20, 20, 40) |
| $^{176}$Lu | (7, 26) | (10, 10) |
| $^{54}$Mn | (7, 26) | (50, 50) |
| $^{99}$Mo | (7, 26, 50) | (20, 20, 40) |
| $^{22}$Na | (7, 26, 50, 82) | (30, 30, 20, 20) |
| $^{99m}$Tc | (7, 26) | (10, 10) |
| $^{203}$Ti | (7, 26) | (40, 40) |
| $^{88}$Y | (7, 26, 50, 82) | (50, 50, 50, 50) |
| $^{65}$Zn | (7, 26, 50, 82) | (30, 30, 30, 30) |

According to one embodiment, the algorithm was tuned to identify the same radio-nuclides with the addition of $^{51}$Cr, $^{68}$Ge, $^{153}$Sm, $^{177m}$Lu, $^{133}$Xe, $^{58}$Co, $^{18}$F, $^{75}$Se, and $^{169}$Yb. This creates a significant challenge as a number of radio-nuclides are difficult to distinguish (e.g., $^{18}$F <–> $^{22}$Na, $^{131}$I <–> $^{133}$Ba, $^{137}$Cs <–> highly shielded $^{241}$Am). The shielding ranges for each radio-nuclide in the library was also increased significantly to ensure that the algorithm covered new material not previously tested. The Bayesian prior was swept over the range to find a good tradeoff between inclusion and exclusion errors. The error rate on the test was 112 inclusion errors and 22 exclusion errors. A total of 109 errors contained one or more errors and thus the overall error rate was 11%. Run time for the branch and bound algorithm was significantly longer (roughly an hour) than the heuristic GADRAS algorithm (less than 2 minutes), but following the initial evaluation, significant speed improvements were made which reduced this considerably. Most samples took less than a second while searching around 100 nodes, but some mixtures were much more challenging requiring thousands of nodes to be searched. This non-deterministic behavior is typical for branch and bound algorithms. The quadratic solver and inequality estimator can be operated with time periods roughly comparable to heuristic methods.

It appears that spectral identification mixture problems can be solved, e.g., unknown radio-nuclides can be identified from a mixture of radio-nuclides, using the branch and bound algorithm with Bayesian priors, according to some preferred embodiments. The performance of this algorithm is far better than any algorithm previously reported. The runtime is sometimes longer than tradition heuristic methods, but still within human tolerance for real-time analysis, and therefore highly applicable to field deployment in handheld analyzers, laboratory scale equipment, etc.

Figure 2:
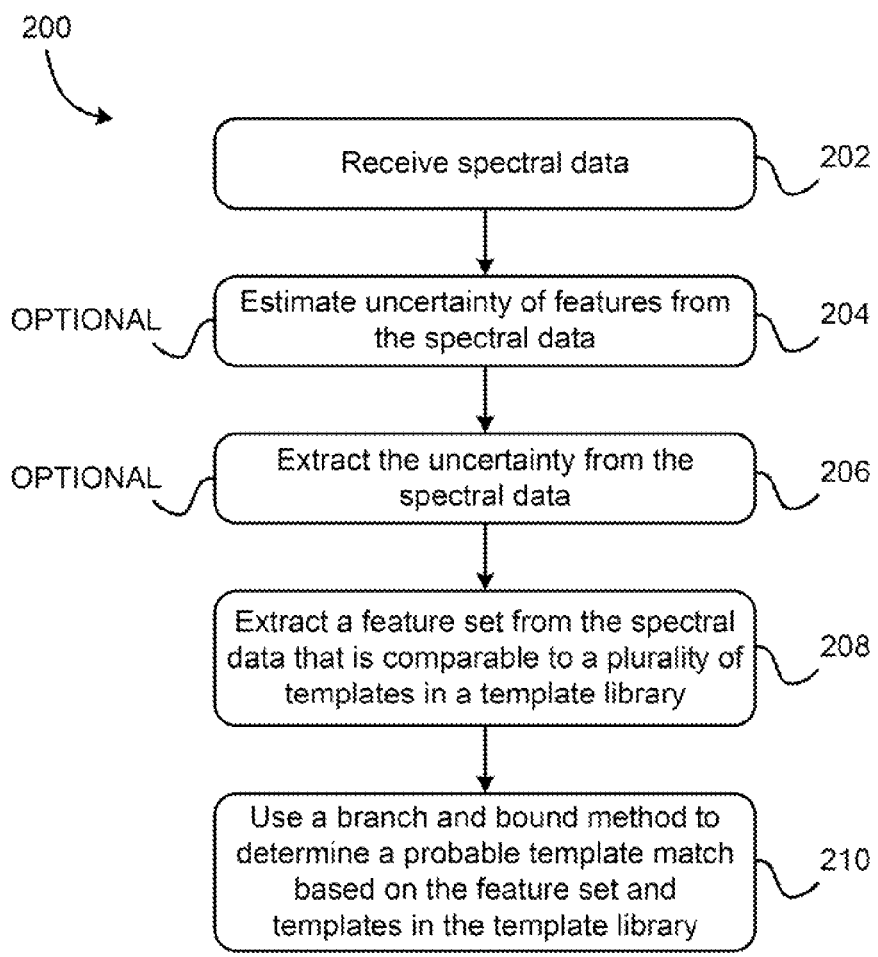
FIG. 2 is a flowchart of a method for identifying one or more radio-nuclides, according to one embodiment.

Referring now to FIG. 2, a method 200 for identifying one or more radio-nuclides is shown according to one embodiment. The method 200 may be carried out in any desired environment, and may include embodiments and/or descriptions not specifically described below, but included previously. In addition, the method 200 may be embodied in a device capable of analyzing spectral data and producing an alert or alarm indicating the presence of one or more types of chemicals, such as explosives, radioactive material, etc.

In operation 202, spectral data is received. The spectral data may be collected from by any device capable of doing so, such as a multi-channel analyzer, a scintillator, etc. In addition, the spectral data may be stored to computer readable medium, and transferred from such medium to be received.

In optional operation 204, uncertainty of features is estimated from the spectral data. Any algorithm for extracting uncertainty may be used, including any of the methods for which the uncertainty can be estimated that have been described previously. For example, Gaussian statistics may be applied, in order to determine the uncertainty in the measuring device and/or spectral data received.

In optional operation 206, the uncertainty is extracted from the spectral data. Any method to extract the uncertainty may be used, including those described previously. Any of these methods may be used to extract uncertainty in optional operation 206. This extraction of uncertainty helps to normalize the data such that a more accurate comparison can take place.

In one embodiment, extracting uncertainty of features from the spectral data may depend on assuming that the spectral data has Poisson statistics and other systematic error, as represented by $$V_i = 1 + F_i + kF_i^2 + \sum_{i=1}^{MAX} q_{(i,j)} F_j,$$

where $V_i$ is variance for a particular feature set, $F_i$ is counts in a feature, k is an adjustable factor, and $q_{(i,j)}$ is used to quantify cross feature variance.

In operation 208, a feature set is extracted from the spectral data that is comparable to a plurality of templates in a template library. For example, a feature set may include a broad range of indicative and/or identifying information therein. The plurality of templates in the template library may include feature sets that are indicative of one or more radio-nuclides, such that a comparison between the extracted feature set and the one or more templates from the template library provides for one or more possible chemical combinations that may be represented by the feature set, as indicated by the closest fitting templates.

In operation 210, a branch and bound method is used to determine a probable template match based on the feature set and templates in the template library. The branch and bound method has been described in detail previously, according to several embodiments, and any of those embodiments may be used in operation 210.

In one embodiment, using a branch and bounds method to determine a probable template match may comprise applying a fitting routine to the extracted feature set, and determining a least mean squared solution subject to non-negative constraints that minimizes an error between the feature set and a linear combination of the templates to determine a probable template match.

In addition, in using a branch and bound method, a Bayesian estimator may be calculated, a probability that the at least one template from the template library having a least error fit to the extracted feature set and the extracted feature set are similar may be determined based on the Bayesian estimator, and the at least one template from the template library that is most similar to the extracted feature set based on the least error fit and the probability may be chosen. In this way, if the spectral data received includes a mixture of contributors, then the method may choose more than one template from the template library which has been determined to contribute to the spectral data received.

In another embodiment, determining a least mean squared solution subject to non-negative constraints may comprise solving for a set of coefficient vectors such that $$F(u) = \sum_i u_i A_i x_i,$$

where $F(u)$ is an expected spectrum, $u_i$ are binary inclusion variables (either 1 or 0), $x_i$ are a set of nuisance parameters, and $A_i$ is a matrix which stores templates for a given radio-nuclide $N_i$, which minimizes $H(u\ x)$. $H(u, x)$ may be expressed as $$H(u, x) = \frac{1}{2}(Y - F(u))^T \sum^{-1} (Y - F(u)) - Q(u),$$

where $Q(u)$ is probability of a mixture, $\Sigma$ is variance expressed as a covariance matrix of each feature in the feature set, and Y is.

Furthermore, if the nuclides are each independent, in some approaches, $$Q(u) = \sum_i u_i \ln P(N_i) + (1 - u_i) \ln(1 - P(N_i)),$$

where $P(N_i)$ is a probability of the radio-nuclide $N_i$ being in the solution. Conversely, if not all of the nuclides are independent, $Q(u)$ is the product of an independent portion, $$\sum_i u_i \ln P(N_i) + (1 - u_i) \ln(1 - P(N_i)),$$

and a dependent portion, the dependent portion being stored end evaluated using a Bayesian Network.

Many of the above described embodiments are useful in many different kinds of systems. In one embodiment, the methods described above may be used in a radiation detection system including a multichannel analyzer and a processing unit. In more embodiments, the methods may be used in a chemical sensing unit including a spectrometer.

The descriptions herein are presented to enable any person skilled in the art to make and use the invention and are provided in the context of particular applications of the invention and their requirements. Various modifications to the disclosed embodiments will be readily apparent to those skilled in the art and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

In particular, various embodiments of the invention discussed herein may be implemented using the Internet as a means of communicating among a plurality of computer systems. One skilled in the art will recognize that the present invention is not limited to the use of the Internet as a communication medium and that alternative methods of the invention may accommodate the use of a private intranet, a Local Area Network (LAN), a Wide Area Network (WAN), or other means of communication. In addition, various combinations of wired, wireless (e.g., radio frequency), and optical communication links may be utilized.

The program environment in which one embodiment of the invention may be executed illustratively incorporates one or more general-purpose computers or special-purpose devices such hand-held computers. Details of such devices (e.g., processor, memory, data storage, input and output devices) are well known and are omitted for the sake of clarity.

It should also be understood that the techniques of the present invention might be implemented using a variety of technologies. For example, the methods described herein may be implemented in software running on a computer system, or implemented in hardware utilizing either a combination of microprocessors or other specially designed application specific integrated circuits, programmable logic devices, or various combinations thereof. In particular, methods described herein may be implemented by a series of computer-executable instructions residing on a storage medium such as a physical computer-readable medium. In addition, although specific embodiments of the invention may employ object-oriented software programming concepts, the invention is not so limited and is easily adapted to employ other forms of directing the operation of a computer.

The invention can also be provided in the form of a computer program product comprising a physical computer readable medium having computer code thereon. A computer readable medium can include any physical medium capable of storing computer code thereon for use by a computer, including optical media such as read only and writeable CD and DVD, magnetic memory, semiconductor memory (e.g., FLASH memory and other portable memory cards, etc.), etc. While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

For example, in one embodiment, a computer program product for identifying one or more unknown radio-nuclides includes a computer readable storage medium having computer readable code stored thereon. The computer readable code comprises computer readable code configured to receive spectral data, computer readable code configured to extract a feature set from the spectral data comparable to a plurality of templates in a template library, and computer readable code configured to use a branch and bound method to determine a probable template match based on the feature set and templates in the template library.

Of course, any of the previously described embodiments, methods, and approaches, may be implemented in computer readable code and be integrated into the computer program product described above.

What is claimed is:
1. A method, the method comprising:
receiving spectral data;
extracting a feature set from the spectral data comparable to a plurality of templates retrieved from a template library stored on a non-transitory computer readable medium;

using a processor to perform a branch and bound method to determine a probable template match based on the feature set and templates in the template library; and outputting the determined probable template match.

2. The method of claim 1, further comprising:

estimating uncertainty of features from the spectral data;

extracting the uncertainty from the spectral data, and identifying one or more radio-nuclides from the spectral data based at least in part on the probable template match.

3. The method of claim 2, wherein extracting uncertainty of features from the spectral data depends on assuming that the spectral data has Poisson statistics and other systematic error, as represented by $$V_i = 1 + Y_i + kY_i^2 + \sum_{j=1}^{MAX} q_{(i,j)} Y_j,$$

where $V_i$ is variance for a particular feature set, $Y_i$ is counts in a feature, k is an adjustable factor, and $q_{(i,j)}$ is used to quantify cross feature variance.

4. The method of claim 1, wherein using a branch and bounds method to determine a probable template match comprises:

applying a fitting routine to the extracted feature set; and determining a least mean squared solution subject to non-negative constraints that minimizes an error between the feature set and a linear combination of the templates to determine a probable template match.

5. The method of claim 4, wherein determining a least mean squared solution subject to non-negative constraints comprises solving for a set of coefficient vectors such that $$F(u) = \sum_i u_i A_i \underline{x}_i,$$

where $F(u)$ is an expected spectrum, $u_i$ are binary inclusion variables (either 1 or 0), $x_i$ are a set of nuisance parameters, and $A_i$ is a matrix which stores templates for a given radio-nuclide $N_i$, which minimizes $H(u, x)$, expressed as $$H(u, x) = \frac{1}{2}(Y - F(u))^T \sum^{-1} (Y - F(u)) - Q(u),$$

where $Q(u)$ is probability of a mixture, $\Sigma$ is variance expressed as a covariance matrix of each feature in the feature set, and Y is a vector of observed features.

6. The method in claim 5, wherein if the nuclides are each independent, $$Q(u) = \sum_i u_i \ln P(N_i) + (1 - u_i) \ln(1 - P(N_i)),$$

where $P(N_i)$ is a probability of the radio-nuclide $N_i$ being in the solution.

7. The method in claim 5, wherein if not all of the nuclides are independent, $Q(u)$ is the product of an independent portion, $$\sum_i u_i \ln P(N_i) + (1 - u_i) \ln(1 - P(N_i))$$

and a dependent portion, the dependent portion being stored and evaluated using a Bayesian Network.

8. A device comprising:

a processor;

a multi-channel analyzer; and a medium operatively coupled to the processor, the medium having computer readable code stored thereon, wherein the computer readable code comprises:

computer readable code configured to receive spectral data;

computer readable code configured to extract a feature set from the spectral data comparable to a plurality of templates in a template library; and computer readable code configured to use the processor to perform a branch and bound method to determine a probable template match based on the feature set and templates in the template library.

9. The device of claim 8, further comprising:

computer readable code configured to estimate uncertainty of features from the spectral data; and computer readable code configured to extract the uncertainty from the spectral data; and computer readable code configured to identify one or more radio-nuclides from the spectral data based at least in part on the probable template match.

10. The device of claim 9, wherein the computer readable code configured to extract the uncertainty from the spectral data depends on assuming that the spectral data has Poisson statistics and other systematic error, as represented by $$V_i = 1 + F_i + kF_i^2 + \sum_{i=1}^{MAX} q_{(i,j)} F_j,$$

where $V_i$ is variance for a particular feature set, $F_i$ is counts in a feature, k is an adjustable factor, and $q_{(i,j)}$ is used to quantify cross feature variance.

11. The device of claim 8, wherein the computer readable code configured to use a branch and bound method comprises:

computer readable code configured to apply a fitting routine to the extracted feature set; and computer readable code configured to determine a least mean squared solution subject to non-negative constraints that minimizes an error between the feature set and a linear combination of the templates to determine a probable template match.

12. The device of claim 11, wherein the computer readable code configured to determine a least mean squared solution subject to non-negative constraints comprises:

computer readable code configured to solve for a set of coefficient vectors such that $$F(u) = \sum_i u_i A_i \underline{x}_i,$$

where $F(u)$ is an expected spectrum, $u_i$ are binary inclusion variables (either 1 or 0), $x_i$ are a set of nuisance parameters, and $A_i$ is a matrix which stores templates for a given radio-nuclide $N_i$, which minimizes $H(u, x)$, expressed as $$H(u, x) = \frac{1}{2}(Y - F(u))^T \sum^{-1} (Y - F(u)) - Q(u),$$

where $Q(u)$ is the probability of the mixture, $\Sigma$ is variance expressed as a covariance matrix of each feature in the feature set, and Y is a vector of observed features.

13. The device of claim 12, wherein if the nuclides are each independent, $$Q(u) = \sum_i u_i \ln P(N_i) + (1 - u_i)\ln(1 - P(N_i)),$$

where $P(N_i)$ is a probability of the radio-nuclide $N_i$ being in the solution.

14. The device of claim 12, wherein if not all of the nuclides are independent, Q(u) is a product of an independent portion, $$\sum_i u_i \ln P(N_i) + (1 - u_i)\ln(1 - P(N_i))$$

and a dependent portion, the dependent portion being stored and evaluated using a Bayesian Network.

15. A computer program product comprising:
a non-transitory computer readable storage medium having computer readable code stored thereon, the computer readable code comprising:
computer readable code configured to receive spectral data;
computer readable code configured to extract a feature set from the spectral data comparable to a plurality of templates in a template library; and
computer readable code configured to use a branch and bound method to determine a probable template match based on the feature set and templates in the template library.

16. The computer program product of claim 15, further comprising:
computer readable code configured to estimate uncertainty of features from the spectral data; and
computer readable code configured to extract the uncertainty from the spectral data; and
computer readable code configured to identify one or more radio-nuclides from the spectral data based at least in part on the probable template match.

17. The computer program product of claim 16, wherein the computer readable code configured to extract the uncertainty from the spectral data depends on assuming that the spectral data has Poisson statistics and other systematic error, as represented by $$V_i = 1 + F_i + kF_i^2 + \sum_{i=1}^{MAX} q_{(i,j)} F_j,$$

where $V_i$ is variance for a particular feature set, $F_i$ is counts in a feature, k is an adjustable factor, and $q_{(i,j)}$ is used to quantify cross feature variance.

18. The computer program product of claim 15, wherein the computer readable code configured to use a branch and bound method comprises:
computer readable code configured to apply a fitting routine to the extracted feature set; and
computer readable code configured to determine a least mean squared solution subject to non-negative constraints that minimizes an error between the feature set and a linear combination of the templates to determine a probable template match.

19. The computer program product of claim 18, wherein the computer readable code configured to determine a least mean squared solution subject to non-negative constraints comprises computer readable code configured to solve for a set of coefficient vectors such that $$F(u) = \sum_i u_i A_i x_i,$$

where $F(u)$ is an expected spectrum, $u_i$ are binary inclusion variables (either 1 or 0), $x_i$ are a set of nuisance parameters, and $A_i$ is a matrix which stores templates for a given radio-nuclide $N_i$, which minimizes H(u, x), expressed as $$H(u, x) = \frac{1}{2}(Y - F(u))^T \sum^{-1} (Y - F(u)) - Q(u)$$

where Q(u) is a probability of a mixture, $\Sigma$ is variance expressed as a covariance matrix of each feature in the feature set, and Y is a vector of observed features.

20. The computer program product of claim 19, wherein if the nuclides are each independent, $$Q(u) = \sum_i u_i \ln P(N_i) + (1 - u_i)\ln(1 - P(N_i))$$

where $P(N_i)$ is a probability of the radio-nuclide $N_i$ being in the solution.

21. The computer program product of claim 19, wherein if not all of the nuclides are independent, Q(u) is a product of an independent portion, $$\sum_i u_i \ln P(N_i) + (1 - u_i)\ln(1 - P(N_i)),$$

and a dependent portion, the dependent portion being stored and evaluated using a Bayesian Network.

* * * * *